United States Patent [19]

Choyke et al.

[11] Patent Number: 5,100,646

[45] Date of Patent: Mar. 31, 1992

[54] NMR GLOMERULAR FILTRATION TEST

[75] Inventors: Peter L. Choyke, Bethesda; Joseph A. Frank, Potomac; Howard A. Austin, Bethesda, all of Md.

[73] Assignee: The United States of America as represented by the Secretary of the Department of Health and Human Services, Washington, D.C.

[21] Appl. No.: 557,038

[22] Filed: Jul. 25, 1990

[51] Int. Cl.$^5$ .................. G01N 31/00; G01N 24/00; A61K 31/28; A61K 31/19

[52] U.S. Cl. .................................. 424/9; 424/4; 514/492; 514/574; 514/836; 514/869; 436/173

[58] Field of Search ............... 424/4, 9; 514/492, 574, 514/836, 869; 128/653 A, 653 C, 654; 436/173

[56] References Cited

U.S. PATENT DOCUMENTS 4,667,447  3/1987  Gries et al. ........................... 424/9

OTHER PUBLICATIONS

Klopper, J. F. et al., J. Nucl. Med. 13(1):107–10 (1972) [In Chem. ABS. 76:109977b (1972).]
SZAxiklas, J. J. et al., J. Nucl. Biol. Med. 15(4):122–5 (1971) [In Chem. ABS. 78:26043b (1971).]
Weinmann, H. J. et al., Physiol. Chem. Phys. Med. NMR 16(2):167–72 (1984) [In Chem. ABS. 101:226159z (1984)].
Koenig, S. H. et al., Invest. Radiol. 21(9):697–704 (1986) [In Chem. ABS. 105:222045u (1986)].

Primary Examiner—Glennon H. Hollrah
Assistant Examiner—Gary E. Hollinden
Attorney, Agent, or Firm—Lowe, Price, Leblanc & Becker

[57] ABSTRACT

A method of determining the glomerular filtration rate of a subject comprises (1) obtaining a serum sample $S_{pre}$ and a urine sample $U_{pre}$ from a subject; (2) administering to the subject an amount of a paramagnetic substance that is filtered by the kidneys and is readily detectable by NMR in serum and urine; (3) allowing for the concentration of the substance to equilibrate between the blood and the extravascular spaces; (4) separating an aliquot of the urine sample $v_A$ and obtaining a serum sample from the subject at the time $t_A$; (5) calculating a urine rate $(v/a)_A$ from the formula $(v/a)_A = V_A/a_A$; (6) measuring the magnetic resonance relaxation times of the serum and urine samples, (7) obtaining the concentrations of the paramagnetic substance in the serum samples and the urine samples by comparing their relaxation times to a standard; and (8) calculating GFR from the formula $$GFR = \sum_{i=0}^{p} 2 \times [PS]_{U_{i+1}} \times v_{i+1}/([PS]_{S_i} + [PS]_{S_{i+1}})/p.$$

16 Claims, No Drawings

NMR GLOMERULAR FILTRATION TEST

TECHNICAL FIELD

This invention relates to a method of determining the glomerular filtration rate (GFR) of a subject that comprises comparing the T1 relaxation rate values of serum and urine samples obtained from a subject given an NMR detectable paramagnetic substance, e.g., Gd-DTPA, that is filtered by the kidney in accordance with a specified formula. More particularly, this invention provides a method which compares the T1 values before and after the administration of the paramagnetic substance to a patient. The present method is safe to the patient and the health practitioner administering it, extremely accurate and easy to perform.

BACKGROUND ART

A determination of the glomerular filtration rate (GFR) of a patient is frequently requested by physicians to assess renal function. Accurate GFR determinations are important in the appropriate dosing of medication as well as for monitoring of drug induced nephrotoxicity in a patient.

Presently, the most frequently measured parameters indicative of renal function are serum creatinine and urea levels. However, much renal damage must occur before these values become abnormal and early detection is therefore not possible. Although the creatinine clearance test is simple and does not require specialized equipment it is subject to important and well recognized errors, some of which are described below.

The accuracy of glomerular filtration rate (GFR) measurements depends on a "filtration" marker. An ideal filtration marker would be one that is exclusively filtered by the kidney but is neither secreted nor reabsorbed by the renal tubules. Creatinine does not comply with all these requisites. While being filtered by the patient's kidneys, it is also secreted by it. Thus, the glomerular filtration rates obtained by this method are inaccurate.

Urine samples for the creatinine clearance test are typically collected for 24 hours. This is a long period of time that is burdensome to the patient and to the nursing staff and at the same time presents repeated opportunities for error. For example, the patient may forget to save one or more samples, and samples may be spilled and specimens or collection time points may be inaccurately recorded by the staff. These limitations of the creatinine clearance method have led nephrologists to rely on other techniques.

An early alternative was the utilization of inulin for measuring glomerular filtration rates (GFR). Inulin is a natural polysaccharide that is exclusively filtered by the kidney. A world-wide shortage of inulin, however, combined with the cumbersome analysis techniques required by the test have prompted the use of other methods.

An alternative test utilizing Technetium-DTPA (Tc-DTPA) as a filtration marker was introduced. Instead of relying on a chemical assay, such as in the case of the creatinine and inulin tests, the Tc-DTPA test relies on the measurement of radioactivity levels in a sample. While the Tc-DTPA test has proven to be accurate, there are various disadvantages to its implementation. The Tc-DTPA test must be performed in an approved nuclear medicine facility by a registered nuclear technologist. In addition, the material administered to the patient is radioactive and the patient is, therefore, exposed to a small dose of radioactivity. These drawbacks have led to a consideration of other techniques.

Gadolinium-DTPA (Gd-DTPA) is a paramagnetic substance (Magnevist, Berlex Laboratories, Cedar Knolls, N.J.) that was approved in the United States as a magnetic resonance imaging contrast agent in 1988. Since then it has been used as an enhancer of magnetic resonance images in tomography studies (U.S. Pat. No. 4,647,447, the entire content of which is incorporated herein by reference). Gd-DTPA has proven to be an extremely safe and well tolerated agent and has been approved for use in children.

Paramagnetic substances such as Gd-DTPA, however, have never been applied to the measurement of glomerular filtration rates by NMR technology up to the present time.

DISCLOSURE OF THE INVENTION

This invention relates to a method of determining the glomerular filtration rate (GFR) of a subject, comprising (1) obtaining a serum sample $S_{pre}$ and a urine sample $U_{pre}$ from a subject;

(2) administering to the subject an amount of a paramagnetic substance that is filtered by the kidneys and is readily detectable by NMR in serum and urine;

(3) allowing for the concentration of the substance to equilibrate between the blood and the extravascular spaces;

(4) allowing the subject to void and discard the urine at a time $t_A$, wherein A is 0;

(5) obtaining a serum sample $S_A$ at the time $t_A$, wherein A is as described above;

(6) making $A = A + 1$;

(7) allowing the subject to void at a time $t_A$ and measuring the voided volume of urine $v_A$, wherein $v_A$ corresponds to a time interval $a_A = (t_A - t_{A-1})$;

(8) separating an aliquot of the urine sample $v_A$ and obtaining a serum sample from the subject at the time $t_A$;

(9) calculating a urine rate $(v/a)_A$ from the formula $$(v/a)_A = v_A/a_A;$$

(10) repeating steps (6) through (9) until the difference among at least three of the urine rates (v/a) is less than about 2 cc/min, and determining the $T1^{Si}$ and $T1^{Ui}$ magnetic resonance relaxation times of the serum and urine samples corresponding to the three end time points $t_A$, wherein i is 0 to p, and p is at least three;

(11) obtaining the concentrations of the paramagnetic substance $[PS]_{Si}$ in the $S_i$ serum samples and the $[PS]_{Ui}$ in the $U_i$ urine samples, wherein i is as defined above, by comparing their relaxation rate $T1^{Si}$ and $T1^{Ui}$ to a standard; and

(12) calculating GFR from the formula $$GFR = \sum_{i=0}^{p} 2 \times [PS]_{Ui+1} \times v_{i+1}/([PS]_{Si} + [PS]_{Si+1})/p,$$

wherein p is as described above.

This invention also relates to a kit for determining GFR with an NMR apparatus, comprising 1-1000 NMR well counter tubes;

at least 1 and up to 10 aqueous standard solutions comprising different concentrations of a pharmaceutically-acceptable paramagnetic substance, each solution having a concentration such that when a specified volume thereof is added to a predetermined volume of control sample it yields an about 0.05 to 0.35M final concentration of the substance, each standard solution being contained in a separate enclosed container;

1-1000 data collection sheets; and a pharmaceutically-acceptable sterile aqueous solution comprising about 0.01 to 0.10M of the paramagnetic substance.

A more complete appreciation of the invention and many of the attendant advantages thereof will be readily perceived as the same becomes better understood by reference to the following detailed description when considered in connection with the following.

BEST MODE FOR CARRYING OUT THE INVENTION

Gadolinium-DTPA (Gd-DTPA.) is exclusively filtered by the kidney and, in addition, it is neither secreted nor reabsorbed by the patient's kidneys. Gadolinium (Gd), in addition, is not a radioactive element and does not expose a patient to radioactivity. It is thus an ideal "filtration marker". Moreover, gadolinium affects the relaxivity of fluids to which it is added.

The present method, thus, relies on the measurement of relaxivity instead of radioactivity as is the case with the Tc-DTPA test. Relaxivity is a property of all fluids, including urine and serum. The relaxivity of a fluid is altered by the addition of Gd and its derivatives. The T1 relaxation time of a fluid can be determined with NMR technology. This value may be used as a measure of a fluid's relaxivity and is directly and linearly proportional to the concentration of a paramagnetic substance such as Gd present in a sample. In the present method, T1 is proportional to the concentration of Gd-DTPA in the sample within certain limits.

The method of the invention may suitably be applied to the field of clinical medicine. Some of its unique and novel features are as follows.

(1) It is performed by administering to a patient a non-radioactive, safe, FDA-approved paramagnetic compound, such as Gd-DTPA.

(2) It may be performed easily in an outpatient hospital facility, a doctor's office, or the patient's home.

(3) It does not require any special treatment of specimens.

(4) It requires relatively simple equipment such as an NMR spectrometer.

(5) The entire procedure is not labor intensive and may be performed by a nurse or other allied health worker with only minimal training.

(6) The results of the test are available within hours. Thus, it is speedy and may help reduce hospital expenditures.

(7) It takes less time, is more accurate, and less inconvenient to perform than the creatinine clearance test.

(8) It is conducted with a simple kit that is not radioactive and therefore safe to handle.

These advantages make the present technology extremely suitable for widespread use in an accurate and inexpensive fashion.

This invention thus provides a method of determining the glomerular filtration rate (GFR) of a subject, which comprises (1) obtaining a serum sample $S_{pre}$ and a urine sample $U_{pre}$ from a subject;

(2) administering to the subject an amount of a paramagnetic substance that is filtered by the kidneys that is readily detectable by NMR in serum and urine;

(3) allowing for the concentration of the substance to equilibrate between the blood and the extravascular spaces;

(4) allowing the subject to void and discard the urine at a time $t_A$, wherein A is 0;

(5) obtaining a serum sample $S_A$ at a time $t_A$ wherein A is as described above;

(6) making $A = A + 1$;

(7) allowing the subject to void at a time $t_A$ and measuring the volume of urine $v_A$, wherein $v_A$ corresponds to a time interval $(a_A = t_A - t_{A-1})$;

(8) separating an aliquot of the urine sample $v_A$ and obtaining a serum sample from the subject at the time $t_A$;

(9) calculating a urine rate $(v/a)_A$ from the formula $$(v/a)_A = v_A / a_A;$$

(10) repeating steps (6) through (9) until the difference among at least three of the urine rates (v/a) is less than about 2 cc/min, and determining the $T1^{Si}$ and $T1^{Ui}$ and magnetic resonance relaxation rate times of the serum and urine samples corresponding to the three end time points $t_A$ for the urine rates, wherein i is 0 to p, and p is at least three;

(11) obtaining the concentrations of the paramagnetic substance $[PS]_{Si}$ in the $S_i$ serum samples and the $[PS]_{Vi}$ in the $V_i$ urine samples, wherein i is as defined above by comparing their relaxation rate values $T1^{Si}$ and $T1^{Ui}$ to a standard; and

(12) calculating GFR from the formula $$GFR = \sum_{i=0}^{p} 2 \times [PS]_{Ui+1} \times v_{i+1} / ([PS]_{Si} + [PS]_{Si+1})/p.$$

wherein p is as described above.

Blood and urine samples are obtained from each patient and the serum is then separated from the blood as is known in the art. The samples may be stored until the entire procedure is completed so that all the determinations are made at one time. Alternatively, each sample may be subjected to NMR spectroscopy immediately after being drawn. When stored, the samples are preferably stored at a temperature of about $-70°$ to $10°$ C., and more preferably about $-30°$ to $5°$ C. in closed containers. In order to make the NMR measurements the samples are preferably at room temperature. Suitable paramagnetic substances are pharmaceutically-acceptable compounds or substances that are filtered by the kidneys, preferably exclusively filtered by them, and more preferably compounds or substances that are neither secreted nor reabsorbed by the kidneys. Examples are Gd-DO$_3$A (Squibb, not FAA approved), Gd-DTPA-BMA (Salutar, not FDA approved) and Dysoprosium-DTPA (Salutar, not FDA approved), among others.

A most preferred substance is Gd-diethylenetriaminepentaacetic acid (Gd-DTPA)

The paramagnetic substance is administered to the subject by routes known in the art, preferably intravenously. The paramagnetic substance, e.g., Gd-DTPA is more preferably administered in an amount of about 0.01 to 0.10 mmol/Kg body weight. In a particularly preferred form of the invention the paramagnetic substance is administered in an amount of about 0.02 to 0.08 mmol/Kg body weight. However, amounts of Gd-DTPA or other paramagnetic substances outside of the stated range may also be administered as long as they are detectable by NMR spectroscopy in the serum and urine samples obtained from the subject and a linear correlation is found at that concentration with the T1 values. The paramagnetic substance is administered to a subject subsequent to obtaining the first blood and urine samples, which may, in a particularly preferred embodiment, be used as controls and for the preparation of standards.

After a period of time of about 10 to 120 minutes after administration of the paramagnetic substrate, and preferably 60 to 120 minutes, are allowed to elapse, the patient voids and a further serum sample is obtained, preferably when the subject is capable of voiding. Alternatively, when catheterized, urine samples may be obtained every about 10 to 60 minutes and preferably about 20 to 30 minutes.

It is preferable that the time interval between subsequently obtained serum and urine samples be in general determined by the subject. Suitable are time intervals of about 10 to 60 minutes, and more preferably about 15 to 45 minutes. In order to minimize the number of samples that need to be taken each subject may be requested to void every so many minutes, e.g., 20 minutes.

Once the samples' volumes and the time interval are obtained for each time point they may be recorded on a time sheet. Alternatively, the data may be input into a computer and the computer may then calculate a urine rate or volume:time interval ratio $(v/a)_A$ from the formula $$(v/a)_A = v_A/a_A$$

wherein v, a and A are as defined above.

The patient is then allowed to void again to obtain another urine sample, and another blood sample is obtained and serum separated from it, and steps (5) through (8) described above are repeated until the difference among at least three of the volume:time ratios is less than about 2 cc/min, and preferably less than about 1 cc/min.

The number of time intervals for which the collected urine volume:time interval ratio between sample collections is substantially equivalent is, however, not fixed at 3 or 4. Any number of intervals may be encompassed by the present method. In general, it is observed that having at least three more constant volume:time ratio intervals will suffice to obtain accurate results.

When the at least three time intervals are chosen in accordance with the criterion described above, then the T1 nuclear magnetic resonance relaxation times are determined for the corresponding urine and serum samples with an NMR spectrometer. This yields at least nine T1 values, at least five of which $T1^{Si}$ correspond to serum samples and at least four $T1^{Ui}$ correspond to urine samples, wherein i is 1 to p, and p is at least 3, but may also be chosen to be any value greater than 3, such as 4, 6, 10, and even higher values.

In a preferred embodiment of the method, the T1 measurements are obtained in step (10) at an NMR frequency of about 1 to 600 MHz, and more preferably at a frequency of about 5 to 500 MHz. All T1 measurements are, however, to be made at substantially similar frequencies.

The concentrations of the paramagnetic substance $[PS]_i$ in the $S_i$ serum [samples] and the $[PS]_{vi}$ urine samples may be obtained by subtracting the T1 relaxation rate times of the respective controls (serum $S_{pre}$ and urine $V_{pre}$ samples obtained in the absence of the substance) and/or comparing with the T1 values of standards prepared with the known amounts of the same paramagnetic substance.

In a particularly preferred embodiment, step 10 is conducted by (a) obtaining $T1_{STD}{}^{Sj}$ relaxation times for at least one standard prepared by adding known amounts of Gd-DTPA to aliquots of the serum sample of volume $v_O{}^S$ obtained from the subject, wherein j is at least 1;

(b) obtaining the concentrations in the $S_i$ serum samples, wherein i is 0 to at least 3, by comparing their corresponding $T1^{Si}$ relaxation rate times to the at least one $T1_{STD}{}^{Sj}$ value, wherein j is at least 1;

(c) obtaining $T1_{STD}{}^{Uk}$ relaxation times for at least one standard prepared by adding known amounts of Gd-DTPA to aliquots of the urine sample of volume $V_o{}^U$ obtained from the subject, wherein k is at least 1; and (d) obtaining the concentrations in the $U_i$ urine samples, wherein i is as defined above, by comparing their corresponding $T1^{Ui}$ relaxation rate values to the at least one $T1_{STD}{}^{Uk}$ values, wherein k is as defined above.

The standards prepared in step (a) are prepared by adding known amounts of the paramagnetic substance to aliquots of the $S_{pre}$ serum sample taken prior to the administration of the substance to the subject. This is the serum sample obtained in step (1). Similarly, the urine standards are prepared in step (c) by adding known amounts of the paramagnetic substance to aliquots of the $V_{pre}$ urine sample. Typically, different volumes of a standard solution of the paramagnetic substance, e.g., Gd-DTPA, are added to substantially equal volumes of separate aliquots of the $S_{pre}$ serum and $S_{pre}$ urine samples to a final concentration in the range of, e.g., about 0.05 to 0.35M of the substance. By means of example, different points in a standard curve may be obtained by preparing standards having a final concentration of 0.05, 0.10, 0.15, 0.20, 0.25, 0.30 and 0.35M Gd-DTPA or other paramagnetic substances. However, other concentrations may also be utilized, even concentrations outside this range if necessary as determined by the T1 values obtained for the samples. In general, as is known in the art, the measured variable for standards must be in the range of the variable's values for the samples. In one preferred embodiment one standard is prepared for each of the serum and urine samples obtained at time 0. These standards are calculated to fall near the expected substance's concentrations in the samples. That is, the T1 values of the controls and the samples are in the same range.

Once the standards are prepared and the corresponding T1 relaxation rate times are obtained (steps (a) and (c)), the latter can be utilized to obtain the concentration of Gd-DTPA in the different serum and urine samples (steps (b) and (d)) based on the T1 values from the corresponding standards as is known in the art. These values can also be obtained from graphs where the concentration of the substance's standards in serum and urine are plotted against the corresponding 1/T1 relaxation rate for the standards. The T1 value for a sample is introduced in the graph and the corresponding concentration is obtained by drawing a line perpendicular to the T1 axis and reading from the other axis the value for the concentration at the point where this line meets the standard line or curve. Alternatively, the concentration of the substance in the samples may be obtained from the linear operation corelating concentrations and relaxation rates as is known in the art.

The $[PS]_{Ui}$ and $[PS]_{Si}$ are then utilized along with the $(v_i{}^U/a_i)$ volume:time interval ratios or urine rates selected to calculate the glomerular filtration rate (GFR) of the subject in accordance with the mathematical formula of step (12).

In a particularly preferred embodiment of the method once the concentrations of the paramagnetic substance in the serum and urine samples are obtained, the calculation of the GFR in step (12) may be conducted manually or with a computerized program.

Suitable paramagnetic substances are known in the art (U.S. Pat. No. 4,647,447 to Gries). Particularly preferred are gadolinium compounds, and more preferred is Gd-DTPA. However, other substances are also contemplated herein as described above.

In addition to the steps described above, the method of the invention may further comprise prior to step (1), hydrating a subject with a hydrating solution. In a preferred mode, the hydration step is conducted via the oral route, and more preferably via an intravenous route. However, other modes of administration are also suitable such as oral hydration, or a combination of oral and parenteral hydration as is known in the art.

Following the injection of the paramagnetic substance, hydration may be maintained by, e.g., a combination of oral and intravenous fluids, as dictated by the subjects ability to drink. The fluids may be administered at up to about 300-500 cc/hr as determined by the subject's condition. Physiologically acceptable aqueous solutions may typically include water for oral hydration or any other non-caffeinated fluid containing water (e.g. juices). Suitable intravenous fluids include 5% dextrose in water. Five percent dextrose in ¼ normal saline and 5% dextrose in half normal saline are considered less desirable since the goal of hydration is water diuresis. As is known in the art, pure water intoxication can result in patients who become hyponatremic, usually a result of renal insufficiency and intravascular overload can result from the sole administration of hypotonic preparations.

The amount of fluid administered by either route should approximate 5 cc/kg/hr of body weight to maintain a diuresis of 300-400 cc/hr. This is important for keeping the length of the study short since the timed intervals may also be determined by the rate of urine production, however, in patients unable to tolerate this amount of fluid, lesser amounts of hydration are possible.

When hydration is administered exclusively via the oral or exclusively via the parenteral route. Oral administration may consist of water or non-caffeinated water based drinks, such as juices, in an initial amount of 20 cc/kg body weight with a maintenance of approximately 5 cc/kg/hr body weight. The exclusively intravenous administration of fluid consists preferably of 5% dextrose in water at a rate of 300-500 cc/hour, depending on patient tolerance. However, other components may also be used as the hydration agent as is known in the art.

In still another preferred mode the method is conducted by practicing the hydration step both by the oral and parenteral routes, preferably oral and intravenous routes. Typically, the hydration step may be conducted about 10 to 120 minutes before step (1), and more preferably about 30-60 minutes before that step. However, other time schedules are also suitable.

When practicing the method of the invention the amount of paramagnetic substance administered the subject in step (2) should be sufficient for the detection of the paramagnetic substance in the urine and serum samples prepared as described herein by NMR technology. Typically, the amount of the paramagnetic substance, e.g., Gd-DTPA administered is about 0.01 to 0.1 mole/Kg of body weight of the subject, and more preferably about 0.02 to 0.08 mole/Kg of body weight. However, other amounts of the paramagnetic substance may also be administered as found appropriate.

Also provided herein is a kit for determining the GFR of a subject with an NMR apparatus, comprising
1-1000 NMR well counter tubes;
1-10 aqueous standard solutions comprising different concentrations of the paramagnetic substance, each solution having a Gd-DTPA concentration that when a predetermined volume thereof is added to a predetermined volume of control sample it yields an about 0.05 to 0.35M concentration of the paramagnetic substance;
1-1000 data collection sheets; and
a physiologically-acceptable sterile aqueous solution of the paramagnetic substance comprising about 0.01 to 1.0M of the substance.

A preferred embodiment of the kit comprises 10-500 NMR well counter tubes, and/or 10 to 500 data collection sheets.

In another preferred mode of the invention, the standard solutions of the kit comprise about 0.1 to 0.50M paramagnetic substance, and more preferably 0.05 to 0.40M. Typically, the standard solutions have a concentration of paramagnetic substance that when a small volume thereof is added to a larger aliquot of a control sample they yield final the paramagnetic substance concentrations spread over range where the concentration in the sample is believed to fall. Alternatively, the samples may be diluted so that their concentration of paramagnetic substance falls within the thus produced standard curve.

In still another preferred embodiment, the sterile paramagnetic solution, e.g., the sterile Gd-DTPA solution, comprises about 0.01 to 1.0M of the substance, and more preferably about 0.50M Gd-DTPA. Doses of about 0.01 to 0.2 mmol/kg weight of the patient are suitably administered. Lower concentrations are in general preferred as long as they are detectable in the urine and serum samples by NMR. The accuracy of the results is not affected by the amount of the substance given the subject as shown in the examples.

Typically, the kit may further contain 1 to 1,000 intravenous administration sets, and more preferably 50 to 500 sets. These sets are sterile and are provided in separate enclosed packages. Each set is utilized for one patient and then discarded. The intravenous administration set may comprise a needle, flexible tubing and a container or reservoir from where the hydration solution and/or the Gd-DTPA solution are administered.

In a most preferred embodiment of the invention the kit further comprises a physiologically-acceptable sterile aqueous solution comprising about 5 wt % dextrose.

This last embodiment of the kit of the invention is intended for practicing the method of the invention with the hydration step. The hydration as described above may be conducted via oral or parenteral routes, or both. The physiologically-acceptable sterile aqueous solution is intended for the parenteral hydration of the subject.

The intraveneous administration sets described above may also be utilized. These administration sets may be utilized for the separate administration of the Gd-DTPA solution and the hydration of the patient to a subject. Both administration lines may be left in place until the entire procedure is completed.

Having now generally described this invention the same will be better understood by reference to certain specific examples, which are included herein for purposes of illustration only and are not intended to be limiting of the invention nor any embodiment thereof, unless so specified.

EXAMPLES

Comparison of Methods Using Tc-DTPA and Gd-DTPA

Prior Art Method and Method of the Invention

The following examples provide data on human glomerular filtration rates (GFR) obtained by practicing the method of this invention that relies on the measurement of the clearance of Gd-DTPA (Magnevist, Berlex Laboratories) from the serum and urine of a patient. Results obtained from 40 patients show good correlation with GFR rates determined by prior art methods such as the Tc-DTPA clearance test.

EXAMPLE 1

Preparatory Procedures 35 patients afflicted with renal dysfunction were evaluated at the National Institutes of Health (N.I.H.) under an Institutional Review Board-Approved protocol. The following procedure was followed for all patients in the study.

The evening before the study the patients were given low salt, low protein diets. On the morning of the study intravenous (i.v.) hydration was started through an i.v. line placed in the arm of each patient until an adequate urinary output was established. An initial loading dose of oral fluid supplemented by 5 wt % dextrose in water intravenous fluid to equal approximately 20 ml/kg BW. The hydration was continued by the i.v. administration of 5 wt % dextrose in water (Mcgaw-Kendall Co., Irvine, Calif.) supplemented by oral hydration for approximately 3–4 hours at 300–400 CC/hour. A separate intravenous line for blood drawing was inserted in the arm of the patient and then each patient was transported to the Nuclear Medicine Department at the N.I.H. Intravenous hydration, supplemented by oral hydration when needed, was continued for the duration of the study. Preliminary blood (S1, 10 cc) and urine (U1, 10 cc) samples were obtained prior to applying any further treatment.

EXAMPLE 2

Procedure for obtaining Blood and Urine Samples 1 millicurie Technetium-DTPA and 0.05 mg/kg Gd-DTPA were simultaneously injected intravenously to each patient through the hydration line. A second blood sample (S2, 6 cc) was obtained from each patient after one hour of "equilibrium time." The equilibrium time is the time in which the compounds reach equilibrium between intra- and extra-vascular spaces. Separate blood and urine samples were obtained for each of the measurements taken Technetium scintillation counting and Gadolinium NMR measurements. This set of samples is collectively referred to as blood and urine samples in the following description.

The patient is then encouraged to void. When the patient was next able to void, usually within 20-25 minutes, a third blood sample (S3, 6 cc) and a second urine sample (U2, 10 cc) were obtained for each patient. The volume and time of the interval since the last voiding event was noted.

Each patient was then allowed to rest for another "interval," after which the patient was again encouraged to void and a fourth blood sample (S4, 6 cc) and a third urine sample (U3, 10 cc) were obtained. The volumes and times were recorded, as well.

This process was repeated once again to obtain fifth blood and fourth urine samples (S5, 6 cc and U4, 10 cc). The volume:time ratios or urine rates for the different points obtained were then compared.

If the volume:time ratios or urine rates for the three intervals are comparable, these values are utilized for the calculations and no more data are obtained for the patient. If, however, the volume:time ratios or urine rates are found to differ, further measurements were taken for the patient at additional intervals until at least three comparable volume:time ratios or urine rates were obtained. After the procedure was completed, the intravenous lines were removed and the patient remained free to move around.

EXAMPLE 3

Scintillation Counting of Samples

The Technetium-DTPA labeled samples were counted in a scintillation counter as is known in the art. A Technetium-DTPA clearance rate was calculated from these data in accordance with standard methods known in the art (Licottke, R. R. and Duarte, C. G., "Lab. Protocol and Meth. Meas. Glomer. Filtr Rate and Renal Plasma Flow", in Renal Function Tests: Clinical Lab. Proc. and Diag., Duarte C. G., Ed., Little Brown, Boston, pp. 290-63 (1980)).

EXAMPLE 4A

Relaxation Measurements of Gd

The Gd-DTPA labeled blood samples were centrifuged to separate serum and blood products. They were left in a refrigerator overnight to eliminate the radioactivity present in the blood due to the presence of Tc-DTPA. The half-life of Technetium is about 6 hours and thus it had almost completely decayed in 24 hours.

Serum and urine samples were then measured using a Praxis 10MHz spectrometer with a 90-tau-90 pulse sequence as described by Farrar et al (Farrar et al, in Pulse and Fourier Transform NMR. Intro. Theory and Meth., pp. 18-33, Academic Press, N.Y. (1971)).

Values were obtained at 30 points for tau and then plotted as an exponential curve versus time. The method of the invention relies on an approximate estimation of the actual T1 value of the substance in the sample being measured. Two T1 values were determined for each sample.

The preliminary or pre-injection blood and urine samples were then "doped" with pre-measured aliquots of a specified volume of known Gd concentration. Pre-injection "standards" were thus produced for the urine and serum samples and their T1s were then measured in the manner described above. The data for the different samples were then recorded on data sheets as shown Table 1 below.

TABLE 1
Data Recording Sheet for Each Patent

| Name | Time | Content | Value |
|---|---|---|---|
| S1 | pre | preliminary blood sample | |
| SS1 | pre | blood STD 1 + Gd-DTPA | |
| SS2 | pre | blood STD 2 + Gd-DTPA | |
| S2 | post | blood start Interval 1 | |
| S3 | post | blood end interval 1 | |
| S4 | post | blood end interval 2 | |
| S5 | post | blood end interval 3 | |
| S6 | post | blood end interval 4 | |
| U1 | pre | preliminary urine sample | |
| US1 | pre | urine STD 1 + Gd-DTPA | |
| US2 | pre | urine STD 2 + Gd-DTPA | |
| U2 | post | urine end interval 1 | |
| U3 | post | urine end interval 2 | |
| U4 | post | urine end interval 3 | |
| U5 | post | urine end interval 4 | |

STD: Standard
S6 and U5 only when desired or necessary

EXAMPLE 4

Computation of Results

The numerical T1 values obtained for each patient were entered into worksheets. This can be performed manually on a PC-based pulse programmer for the spectrometer or on a separate computerized system. Existing spreadsheets (Excel, Lotus 1-2-3) can be used although any simple spreadsheet will suffice and may be run on the PC driver of the spectrometer.

Separate concentration vs. 1/T1 lines were derived for the urine and serum samples using a three point best-fit line estimation as is known in the art.

The three points used were the pre-injection values (S1) and (U1), and the two standards (SS1, SS2). Two lines are thus derived, one for urine (U1, US1, US2) and another for serum (S1, SS1, SS2). The concentration of Gd-DTPA may then be derived for the remaining samples (S2-S6, U2-U6).

The thus obtained concentration values are then employed for calculating the GFR as follows.

$$GFR_{average} = [Gd-DTPA]_U \times Urine\ Rate / average[Gd-DTPA]_S$$

wherein the $[Gd-DTPA]_U$ is obtained from the ordinate of the graph for the urine line or by solving for concentration from the equation for least means squares, the average $[Gd-DTPA]_S$ is obtained from the ordinate of the graph for the serum line and by averaging the T1 relaxation times from the serum samples obtained at the beginning and end of each interval $$[Gd]_{Si(ave)} = ([Gd]_{Si} + [Gd]_{Si+1})/2$$

and the urine rate is the urine volume:time interval rate obtained above.

The GFR for, e.g., interval 1, was then calculated as follows.

$$GFR_1 = [U2] \times (urine\ vol/interval\ 1) / ([S2]+[S3])/2$$

The GFRs obtained with the Tc-DTPA clearance method ranged from about 15 to 139 cc/min as shown in Table 2 below.

TABLE 2
GFRs Obtained for Tc-DTPA Clearance and Gd-DTPA Clearance Tests

| PATIENT # | NAME | DATE | Tc GFR | Gd GFR | TcSD | GdSD |
|---|---|---|---|---|---|---|
| 1 | KKY | 9/28/89 | 57.6 | 54.5 | 2.1 | 2.1 |
| 2 | PMS | 9/26/89 | 15.4 | 15.4 | 2.7 | 2.7 |
| 3 | SKB2 | 10/26/89 | 93.4 | 99.5 | 4 | 7.9 |
| 4 | SKB3* | 1/17/90 | 86 | 106 | | |
| 5 | PAB | 9/23/89 | 57.3 | 54.6 | 3.08 | 4.1 |
| 6 | SYL | 9/19/89 | 83.2 | 83.2 | 8.9 | 4.4 |
| 7 | JMK* | 9/15/89 | 139 | 158 | 3.5 | 4 |
| 8 | LDO | 10/13/89 | 100 | 112 | 5.2 | 2.6 |
| 9 | EP | 10/18/89 | 58.9 | 54.4 | 2.6 | 2.3 |
| 10 | MJM | 10/5/89 | 65.2 | 71.6 | 2.6 | 8.7 |
| 11 | DM | 10/5/89 | 83.8 | 77 | 10 | 10.6 |
| 12 | BLG | 10/3/89 | 97.1 | 97.2 | 5.7 | 5.7 |
| 13 | BLG* | 11/1/89 | 88.4 | 74.6 | 19 | 2.5 |
| 14 | BLG | 1/24/90 | 83 | 89 | 20.7 | 32 |
| 15 | RG | 9/27/89 | 87 | 80.3 | 3.1 | 5.4 |
| 16 | RG2 | 12/6/89 | 79.3 | 76.6 | 13.2 | 7.9 |
| 17 | ER2 | 2/7/90 | 93.2 | 99 | 2.7 | 10.6 |
| 18 | KR2 | 1/10/90 | 82.8 | 93.7 | 8.2 | 7.2 |
| 19 | DJB | 10/23/89 | 60 | 65.6 | 1.86 | 1.1 |
| 20 | LEE | 10/20/89 | 83.2 | 86.8 | 3.1 | 5.1 |
| 21 | DAC | 11/8/89 | 54 | 58.9 | 5.7 | 4.7 |
| 22 | DH | 10/25/89 | 74.5 | 72.3 | 3.66 | 8.2 |
| 23 | NM | 10/27/89 | 101 | 110 | 5.5 | 8.4 |
| 24 | JO'B | 11/15/89 | 57.5 | 59 | 4.4 | 2.7 |
| 25 | ER | 11/16/89 | 100.4 | 99.2 | 5.4 | 7.2 |
| 26 | LD | 11/17/89 | 82.1 | 81.3 | 7.9 | 4.7 |
| 27 | LD2 | 12/19/89 | 65.7 | 63 | 1.8 | 4.6 |
| 28 | MM | 11/22/89 | 72.4 | 72.2 | 8.7 | 12.5 |
| 29 | DAC* | 12/14/89 | 100 | 109.7 | | |
| 30 | DC | 2/1/90 | 78.3 | 84.5 | 19.2 | 23.7 |
| 31 | IMS | 12/18/89 | 89.6 | 92.7 | 4.8 | 6.9 |
| 32 | PB | 12/21/89 | 77 | 82.2 | 2.8 | 1.9 |
| 33 | AM | 12/12/89 | 51.8 | 52.3 | 5.1 | 6.2 |
| 34 | DC* | 30 Jan | 93.5 | 102.6 | 3.2 | 3.2 |
| 35 | GA | 1/29/90 | 58.8 | 58.5 | 4 | 4.2 |

The results obtained showed the method of the invention to be an accurate method of determining GFR.

The values obtained with the Tc-DTPA clearance test and the Gd-DTPA clearance test showed a good correlation (R=0.96). These data represent the summation of the GFRs obtained with the Gd-DTPA clearance method of the invention for 10 patients who received 0.1 mmole/kg wt Gd-DTPA and for 30 patients who received 0.05 mmole/kg wt.

The dose of Gd-DTPA administered the patient doe not significantly alter the accuracy of the results. In view of this information keeping the dose as low as the lower dose of Gd-DTPA or even lower may be adopted for further applications.

The invention now being fully described, it will be apparent to one of ordinary skill in the art that many changes and modifications can be made thereto without departing from the spirit or scope of the invention as set forth herein.

We claim:

1. A method of determining the glomerular filtration rate (GFR) of a subject, comprising
   (1) obtaining a serum sample $S_{pre}$ and a urine sample $U_{pre}$ from a subject;
   (2) administering to the subject a diagnostically effective amount of a paramagnetic substance that is filtered by the kidneys and is readily detectable by NMR in serum and urine;
   (3) allowing for the concentration of the substance to equilibrate between the blood and the extravascular spaces;

(4) allowing the subject to void and discard the urine at a time $t_A$, wherein A is 0;

(5) obtaining a serum sample $S_A$ at the time $t_A$, wherein A is as described above;

(6) making $A = A + 1$;

(7) allowing the subject to void at a time $t_A$ and measuring the voided volume of urine $v_A$, wherein $v_A$ corresponds to a time interval $a_A = (t_A - t_{A-1})$;

(8) separating an aliquot of the urine sample $v_A$ and obtaining a serum sample from the subject at the time $t_A$;

(9) calculating a urine rate $(v/a)_A$ from the formula $$(v/a)_A = v_A/a_A;$$

(10) repeating steps (6) through (9) until the difference among at least three of the urine rates (v/a) is less than about 2 cc/min, and determining the $T1^{Si}$ and $T1^{Ui}$ magnetic resonance relaxation rate times of the serum and urine samples corresponding to the three end time points $t_A$, wherein i is 1 to p, and p is at least three;

(11) obtaining the concentrations of the paramagnetic substance $[PS]_{Si}$ in the $S_i$ serum samples and the $[PS]_{Ui}$ in the $U_i$ urine samples, wherein i is as defined above, by comparing their relaxation rate time $T1^{Si}$ and $T1^{Ui}$ to a standard; and

(12) calculating GFR from the formula $$GFR = \sum_{i=0}^{p} 2 \times [PS]_{Ui+1} \times v_{i+1}/([PS]_{Si} + [PS]_{Si+1})/p,$$

wherein p is as described above.

2. The method of claim 1, wherein the paramagnetic substance is Gd-DTPA.

3. The method of claim 1, wherein step (i) is conducted by (a) obtaining $T1_{STD}{}^{Sj}$ relaxation rate times for at least one standard prepared by adding known amounts of Gd-DTPA to aliquots of the serum sample of volume $v_O{}^S$ obtained from the subject, wherein j is at least 1;

(b) obtaining the concentrations of the paramagnetic substance $[PS]_{Si}$ in the $S_i$ serum samples, wherein i is 1 to at least 3, by comparing their corresponding $T1^{Si}$ relaxation rate times to the at least one $T1_{STD}{}^{Sj}$ value, wherein j is at least 1;

(c) obtaining $T1_{STD}{}^{Uk}$ relaxation times for at least one standard prepared by adding known amounts of the paramagnetic substance to aliquots of the urine sample of volume $V_o{}^U$ obtained from the subject, wherein k is at least 1; and (d) obtaining the concentrations of the paramagnetic substance $[PS]_{Ui}$ in the $U_i$ urine samples, wherein i is as defined above, by comparing their corresponding $T1^{Ui}$ relaxation values to the at least one $T1_{STD}{}^{Uk}$ values, wherein k is as defined above.

4. The method of claim 1, further comprising hydrating the subject by parentally administering an aqueous solution comprising about 0.01 to 1.0 g dextrose/1 solution prior to step (1).

5. The method of claim 2, wherein the hydration step is conducted intravenously.

6. The method of claim 1, further comprising
hydrating a patient by orally administering about 10-30 cc water/Kg body weight prior to step (1).

7. The method of claim 4, wherein
the hydration step is conducted about 20 to 120 minutes before step (1).

8. The method of claim 4, further comprising prior to step (1)
further hydrating the subject by orally administering to the patient about 10-30 cc water/Kg body weight.

9. The method of claim 8, wherein
the hydration steps are started about 20 to 120 minutes before step (1).

10. The method of claim 1, wherein
the amount of paramagnetic substance administered the subject in step (2) is about 0.01 to 0.1 mmole/Kg body weight.

11. The method of claim 10, wherein
the amount of paramagnetic substance administered the subject in step (2) is about 0.02 to 0.08 mmol/Kg body weight.

12. The method of claim 1, wherein
the paramagnetic substance is administered in step (2) intravenously.

13. The method of claim 1, wherein
the T1 measurements are obtained at an NMR frequency of about 1 to 600 MHertz and the T1 measurements are obtained at substantially the same frequency.

14. The method of claim 1, wherein
said time intervals separating the time at which said urine and serum samples required by claim 1 are obtained are about 10 to 60 minutes.

15. The method of claim 3, wherein
when a predetermined volume of each of the standards prepared in steps (a) and (b) is added to a predetermined volume of sample in steps (c) and (d) it yields a final concentration of about 0.05 to 0.35M of the paramagnetic substance.

16. The method of claim 1, wherein
the calculation of the GFR in step (9) is conducted with the aid of a computerized program.

* * * * *